United States Patent [19]
Kolenik

[11] 3,983,880
[45] Oct. 5, 1976

[54] APPARATUS FOR GENERATING HEART STIMULATION PULSES UPON DEMAND

[75] Inventor: Steve A. Kolenik, Leechburg, Pa.

[73] Assignee: ARCO Medical Products Company, Leechburg, Pa.

[22] Filed: Oct. 20, 1975

[21] Appl. No.: 624,406

Related U.S. Application Data

[63] Continuation of Ser. No. 337,915, March 5, 1973, abandoned.

[52] U.S. Cl. .......................................... 128/419 PG
[51] Int. Cl.² .......................................... A61N 1/36
[58] Field of Search..... 128/419 P, 419 PG, 419 PS, 128/421, 422, 423; 331/113 R

[56] References Cited
UNITED STATES PATENTS

| | | | |
|---|---|---|---|
| 3,193,782 | 7/1965 | Trojak | 331/113 R |
| 3,406,355 | 10/1968 | Trujillo | 331/113 R |
| 3,431,912 | 3/1969 | Keller, Jr. | 128/419 PG |
| 3,547,127 | 12/1970 | Anderson | 128/419 PG |
| 3,548,831 | 12/1970 | McLean et al. | 128/419 PG |
| 3,600,586 | 8/1971 | Barthelemy et al. | 128/419 PS |
| 3,656,487 | 4/1972 | Gobeli | 128/419 PG |
| 3,693,626 | 9/1972 | Cole | 128/419 PG |
| 3,726,285 | 4/1973 | Bowers et al. | 128/419 PG |
| 3,759,266 | 9/1973 | Lee | 128/419 PG |
| 3,898,994 | 8/1975 | Kolenik et al. | 128/419 PG |

*Primary Examiner*—William E. Kamm
*Attorney, Agent, or Firm*—John C. Martin, Jr.

[57] ABSTRACT

Apparatus for generating electrical stimulation pulses in the absence of naturally occurring "R" heart waves includes a free running multivibrator for generating pulses at the desired heart stimulation rate and an output amplifier and voltage multiplier for amplifying the generated pulses for application to the heart. A plural stage filter-amplifier amplifies any naturally occurring "R" waves to trigger a normally nonconducting multivibrator to activate disabling transistors, in turn, which discharge the timing capacitors of the free running multivibrator.

The apparatus can be used with either a chemical or nuclear battery or other load dependent low voltage source.

8 Claims, 2 Drawing Figures

APPARATUS FOR GENERATING HEART STIMULATION PULSES UPON DEMAND

CROSS-REFERENCES TO RELATED APPLICATIONS

This application is a continuation of copending application Ser. No. 337,915, filed Mar. 5, 1973, and now abandoned.

BACKGROUND OF THE INVENTION

1. Field of the invention.

This invention relates to improvements in apparatus for generating pulses for heart stimulation, and more particularly to improvements in apparatus which generates pulses for heart stimulation in the absence of naturally occurring heart pulses.

2. Description of the prior art.

The living heart effects its pumping action with many complex muscle contractions and relaxations. Typically, such contractions and relaxations are accompanied by electro-chemical potential pulses which can be analyzed and associated with particular heart muscle actions. For example, the contraction of the ventricle heart muscle produces a positive pulse, ordinarily of larger magnitude and time duration than the other heart-produced pulses. Thus, the ventricle muscle contraction presents a unique frequency spectrum which can be detected and distinguished from the other heart-produced pulses.

As a result of disease, injury, or other cause, occasionally a heart fails to function properly; for instance, one or more muscles may fail entirely to properly contract and relax, or may intermittently fail to properly function. In such cases, artificially produced electrical stimulation pulses may be effective in restoring the proper function to the failing muscle.

Many devices have been proposed for generating such pulses to stimulate a naturally occurring heartbeat. The devices which operate to produce stimulation pulses when the heart fails but which otherwise remain quiescent or inactive, such as the device disclosed in U.S. Pat. No. 3,345,990, are commonly referred to as "demand" heart pacers, and generally include one or more electrical conduction leads physically implantable in the heart to detect the presence or absence of the naturally generated electrochemical potential associated with a particular muscular function and apply electrical stimulation pulses to simulate the natural pulses in their absence. Demand pacers such as disclosed in U.S. Pat. No. 3,253,595 have been advanced which are entirely implantable within the body and include solid state circuitry potted in a unit having a surrounding conductive portion to establish electrical contact with the body at a remote point, such as in the abdomen. A single lead is provided for connection to the heart at an appropriate location.

Of the demand heart pacers proposed heretofore, many employ circuits which are continuously conducting, such as monostable multivibrators which switch from a first conducting state, for instance through one transistor, to a second conducting state, through a different transistor. Thus, the multivibrator may draw current continuously from the voltage source, which can shorten its useful lifetime and require frequent replacement and attention.

Additionally, circuits of the prior art commonly employ relatively complicated circuitry to distinguish the various heart pulses, heart pacers commonly being triggered upon the presence or absence of the so-called "QRS" complex heart pulses.

Finally, demand heart pacers have been proposed which employ multivibrator apparatuses to generate periodic heart stimulation pulses at the multivibrator frequency, but upon detection of the triggering naturally occurring heart pulse, such as the QRS complex above mentioned, the output from the multivibrator is switched to a substitute load, the multivibrator being allowed to continue its periodic conduction as if it were still supplying heart stimulation pulses to the heart itself. This also results in current from the supply to flow through the transistors or current regulating devices of the multivibrator and is another source of unnecessary power drain from the supply voltage source.

Becoming of recently increasing interest, nuclear batteries are being employed to supply power to heart pacer circuits. Nuclear batteries, however, present problems in the circuit design not ordinarily encountered in the use of ordinary chemical batteries, the voltage supply, for example, being more dependent upon the impedance of the circuit to which the voltage is applied, and, additionally, being of relatively lower magnitude than a conventional chemical type battery of otherwise same relative characteristics. The use of a nuclear battery, therefore, requires particular circuitry design to obviate these problems.

BRIEF DESCRIPTION OF THE INVENTION

The invention, in its broad aspect, presents a demand heart pacer and includes a pulse generating multivibrator, controlled by plural RC timing circuits to free run at the desired heart stimulation rate. An amplifier amplifies the multivibrator pulses, and, in a preferred embodiment usable with a low voltage nuclear battery power supply or the like, an output voltage doubler is provided to present an output current pulse of sufficient magnitude for heart application.

A multi-stage frequency selective amplifier amplifies heart pulses naturally occurring of a particular frequency spectrum, such as that of "R" waves, to trigger a pulse generator, which, in turn, activates means for discharging the capacitors of the timing circuits of the free running multivibrator each time a natural heart pulse occurs so that no output pulse is generated. The apparatus, therefore, generates a heart stimulation pulse each time the heart fails to do so, but does not generate a stimulation pulse if the heart pulses on its own.

In light of the above, it is an object of the invention to present an apparatus for generating electrical pulses for heart stimulation in the absence of natural heart pulses.

It is another object of the invention to present a demand pacer circuit.

It is still another object of the invention to present a demand pacer circuit which can be utilized with a low voltage nuclear power source.

It is another object of the invention to present a demand pacer circuit which distinguishes and amplifies a naturally occurring heart wave of a particular frequency spectrum and attenuates other naturally occurring heart pulses.

It is still another object of the invention to present a demand pacer circuit which draws a minimum amount of current in operation and which has a quiescent state between pulses.

It is another object of the invention to provide a demand pacer circuit which incorporates a plural stage amplifier for amplifying only naturally occurring "R" pulses.

It is still another object of the invention to present a demand pacer circuit which incorporates a high impedance voltage multiplier output.

It is still another object of the invention to present a demand pacer circuit which incorporates means for testing the circuit in operation without removal from the patient.

It is yet another object of the invention to present a demand pacer circuit which employs a disabling section which discharges the timing capacitors of a free running multivibrator.

BRIEF DESCRIPTION OF THE DRAWING

The invention is illustrated in the accompanying drawing, wherein.

DETAILED DESCRIPTION OF THE PREFERRED EMBODIMENTS

Figure 1:
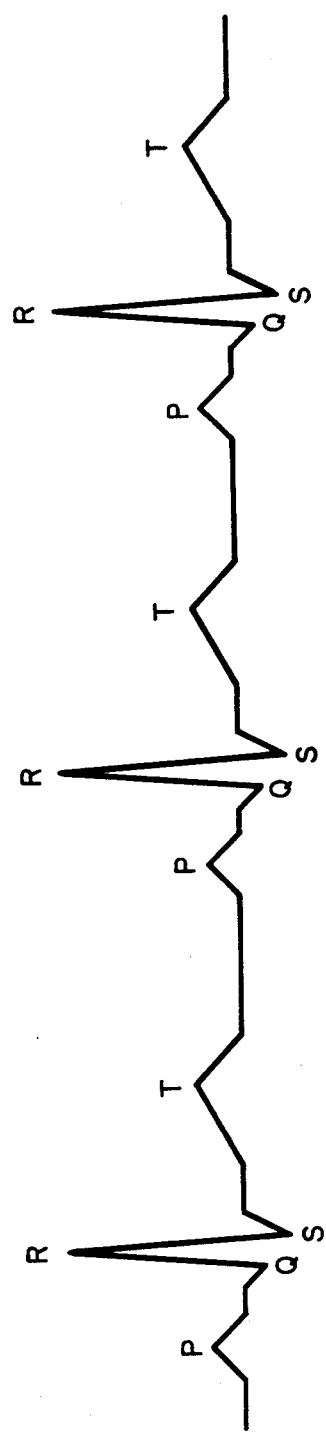
FIG. 1 is a curve showing typical heart generated pulses.

As mentioned above, the normal actions of the pumping muscles of the heart are ordinarily accompanied by identifiable electrical potentials or signals. A typical composite waveform of the signals as a function of time is shown in FIG. 1. Essentially, the contraction of the atrium is accompanied by a "P" wave of positive potential, followed, after a delay known as the "AV" or atrial ventricular delay, by a potential called the "QRS" complex associated with the contraction and relaxation of the ventricle muscle, followed by a "T" wave after a "refractory period". As shown, the "P", "R" and "T" waves are of positive potential and the "Q" and "S" are of negative potential. Depending on the location of the heart connection, however, the respective polarities of the "P", "Q", "R", "S" and "T" may be reversed, which, for example, could be displayed in the manner of the waveform of FIG. 1 with the negative direction upwards. Each has its own frequency spectrum, and, therefore, can be electronically frequency distinguished from the others.

The demand pacer circuitry in accordance with the invention, as below described in detail, is intended primarily to distinguish and detect the existence of a particular naturally occurring heart wave, such as an "R" wave, and to generate a heart stimulation pulse in its absence, but remain quiescent or inactive, not generating a heart stimulating pulse, in its presence. Thus, if the heart to which the stimulation pulses of the circuitry are applied properly generates an "R" wave (or other wave to which the circuit is tuned), the stimulation pulse generating portion of the circuitry will remain quiescent. On the other hand, in the absence of the particular naturally occurring heart pulse, the pacer circuitry will generate the appropriate stimulation pulse.

Figure 2:
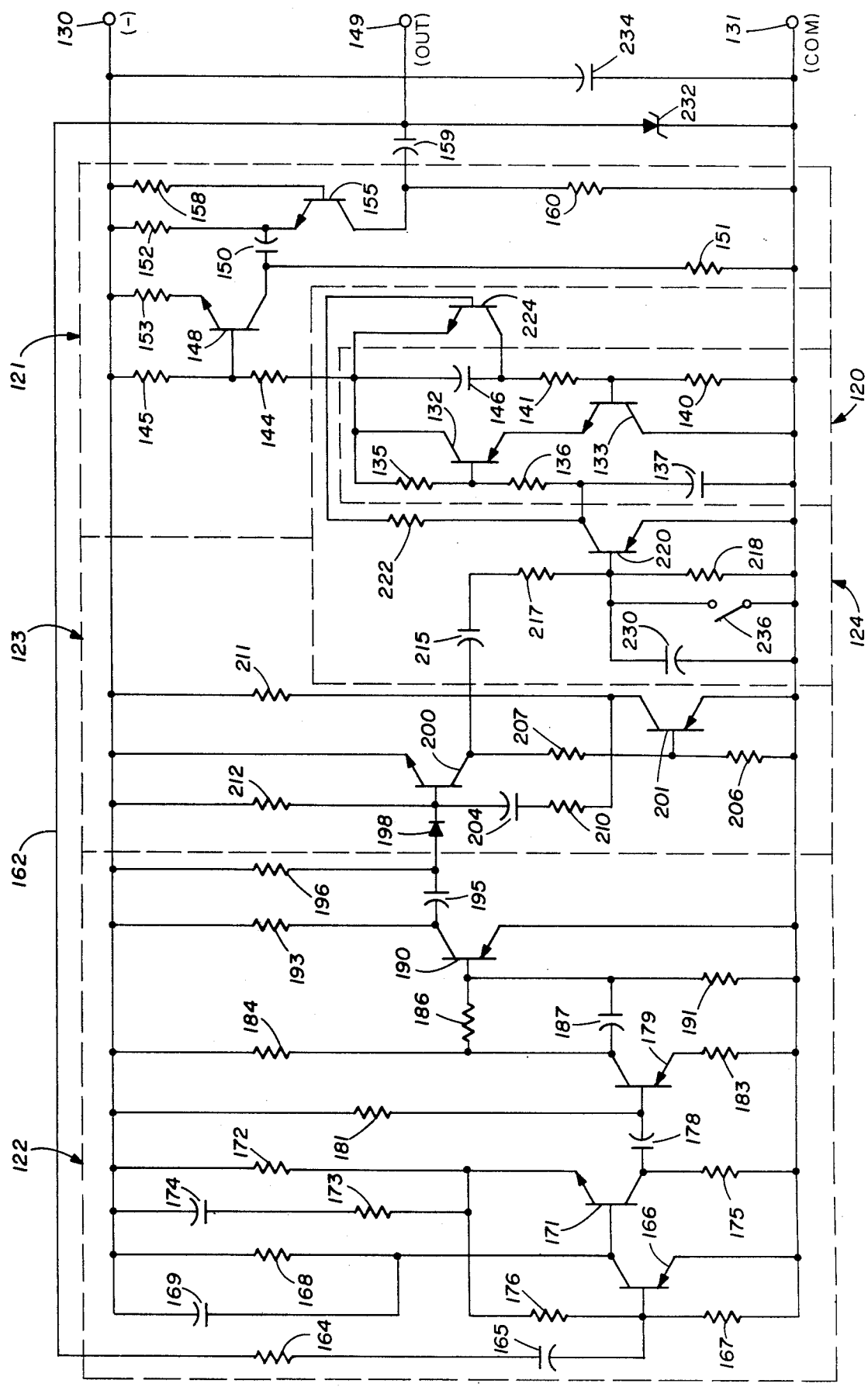
FIG. 2 is a schematic diagram illustrating another preferred embodiment of the pacer circuit, in accordance with the invention, responsive to heart demand, with low voltage supply capability for use with a nuclear battery or voltage source in which the voltage may vary with the load thereupon.

A preferred embodiment of the pacer circuit, in accordance with the invention, for primary utilization with a nuclear potential source or power supply is illustrated in FIG. 2. The circuit includes five main sections, each outlined by dotted lines. A free running multivibrator 120 generates output pulses at the desired application rate to a high impedance voltage multiplier output amplifier 121, which produces an output current pulse for application to the heart. Naturally occurring heart generated pulses are conducted to a frequency filtering amplifier including a four-stage a-c coupled frequency selective amplifier and pulse shaping section 122, where the "R" wave is selectively amplified and shaped and the other pulses of different frequency spectra are attenuated. Each amplified pulse is directed to a normally nonconducting monostable multivibrator (hereinafter referred to merely as a monostable) 123 which is triggered into conduction by the amplified "R" wave to produce an output pulse. The monostable output pulse is then directed to a disabling circuit 124 which discharges the capacitors of the free running multivibrator 120 for one pulse period each time a heart generated "R" wave occurs. The disabling circuit 124 additionally includes a magnetic switch to bypass the transistor control voltage to ground to enable the disabling circuit, free running multivibrator and power source to be tested.

In the circuit embodiment of FIG. 2, terminals 130 and 131 are connected to negative and positive terminals, respectively, of a voltage source or source of electrical potential.

With specific reference to the various sections of the pacer circuit of FIG. 2, the free running multivibrator 120 for the stimulation pulse initiation includes a p-n-p transistor 132 and an n-p-n transistor 133 connected to present a current flow or conduction path through their series connected emitters and collectors, as shown. Means for presenting a time varying voltage level, such as at least one and preferably, as shown, a pair of RC timing circuits control the rate at which the multivibrator pulses, the first timing circuit. The first timing circuit includes series connected resistors 135 and 136, in turn, in series with capacitor 137, the base of transistor 132 being connected between resistors 135 and 136. Likewise, the second RC timing circuit for transistor 133 includes series connected resistors 140 and 141 in series with capacitor 146, the base of transistor 133 being connected between resistors 140 and 141. Thus, in operation, the potential from the source applied at terminals 130 and 131 builds up upon capacitors 137 and 146 until the transistors 132 and 133 become forward biased into conduction. At that point, the voltage upon the capacitors discharges, primarily through the base circuits of their respective transistors until the reduced voltage upon the respective bases of transistors 132 and 133 cause the transistors to fall out of conduction, starting the cycle again.

The values of resistors 135, 136, 140 and 141 and of capacitors 137 and 146 are chosen to cause the multivibrator to generate pulses of sufficient width at a normal heartbeat rate, such as 71 beats per minute. Additionally, the values (exemplars listed below) of the corresponding components, the capacitors 137 and 146, the resistors 135 and 140, and the resistors 136 and 141 of each RC timing circuit are the same. Thus, redundant RC timing networks are presented, which minimize the effects of component value changes in the operation of the circuit. For instance, if the value of the capacitor 137 in one of the RC timing networks were to change, its effects would not drastically change the pulse rate of the multivibrator because of the remaining proper valued capacitor 146 in the other RC network.

In the multivibrator circuit illustrated, the pulse rate is primarily determined by the charging time of the capacitors 137 and 146 as controlled by the values of the capacitor 146 and resistor 140, and by the values of the capacitor 137 and resistor 135 (the values of resistors 136 and 141 being small with respect to the values of the resistors 135 and 140, therefore having little effect on the charge rate of the capacitors 137 and 146). The width of the pulses, on the other hand, is primarily determined by the values of resistors 136 and 141 in conjunction with their respective capacitors 137 and 146. With components as listed below, for example, a pulse repetition rate of approximately 70±5 beats/minute and pulse width of approximately 0.8–1.0 milliseconds can be achieved.

The conduction path defined by conducting transistors 132 and 133 permits current flow through voltage dividing resistors 144 and 145 to present a voltage upon the emitter-base junction of transistor 148 of the output stage 121. The multiplier stage 121, illustrated, acts as a voltage doubler and presents an output current pulse to the output terminal 149. In operation, a voltage in the quiescent state is built up upon capacitor 150 through resistors 151 and 152. When the multivibrator stage 120 permits conduction through resistor 145 forward biasing the base-emitter junction of transistor 148, the voltage upon capacitor 150 is added to the supply voltage from terminal 130 through the collector and emitter of transistor 148 and the emitter resistor 153.

At the time, the base-emitter junction of transistor 155 is also forward biased into conduction, the base voltage of transistor 155 being maintained by the resistor 158, and the collector bias being established through resistor 160 to the positive common terminal 131. The transistor 155 thus presents a current output path through its emitter and collector and d-c isolating capacitor 159 to the output terminal 149 for conduction to the heart through an appropriate heart lead (not shown). The output transistor 155 additionally presents a high output impedance upon the output terminal 149.

If a naturally generated "R" heart wave occurs, it is conducted through the heart lead (not shown) to terminal 149, thence along conductor 162 to the frequency selective amplifier 122. The heart pulses initially are filtered through a resistor 164 connected in series with a capacitor 165 before application to the first amplifier stage. The values of resistor 164 and capacitor 165 are chosen to present a low frequency roll off characteristic to present a high impedance to and partially attenuate low frequency heart waves below the frequency spectrum of the "R" wave.

The capacitor 165 also differentiates the incoming signal. Thus, if a negative pulse is applied to the resistor 164 and capacitor 165, it is differentiated to produce first a negative voltage output corresponding to the rate of the negative voltage increase, followed by a positive pulse, corresponding to the subsequent rate of negative voltage decrease. Therefore, the pacer circuit, responsive to positive "R" signals, as will be apparent below, will respond to a negative input pulse from the heart, since a positive pulse resulting from the capacitor differentiation will nevertheless be applied to the first transistor stage including transistor 166, biased for Class A operation. Thus, the precise location of the electrode implanted in the heart is not critical insofar as it is not required to conduct heart pulses of any particular polarity to the pacer circuit.

The first transistor 166 includes a high frequency roll off collector load impedance, including resistor 168 in parallel with capacitor 169. The emitter-base bias on the first stage transistor 166 is maintained by a resistor 167 to the common terminal 131 and by a resistor 176 to the emitter of the second stage transistor 171, for stabilization.

In operation, capacitor 169 presents a low impedance in the collector lead of transistor 166 at high frequencies, thereby diminishing or reducing the high frequency gain of the first amplifier stage, including transistor 166. On the other hand, at low frequencies, the gain of the first amplifier stage is determined by the resistance of resistor 168, capacitor 169 presenting, essentially, an infinite or very high impedance.

The output from transistor 166 developed across the load resistor 168 is applied to the base of the second stage transistor 171 also biased for Class A operation. In the emitter circuit of transistor 171, a first resistor 172 is connected in parallel with the series connection of a second resistor 173 and a capacitor 174. A load resistor 175 is connected in the collector lead of transistor 171 to the common terminal 131. In operation, at low frequencies, the capacitor 174 presents a high impedance, whereby the resistors 172 and 175 determine the voltage developed across resistor 175 and hence the gain of the second amplifier stage including transistor 171. On the other hand, at high frequencies, the capacitor 174 presents little impedance, thereby connecting resistor 173 in parallel with the resistor 172 to decrease the gain of the second amplifier stage. Thus, the second amplifier stage presents a low frequency roll off to amplify only signals at and above the "R" wave frequency spectrum.

The output of the transistor 171 is developed across a load resistor 175 and is a-c coupled by a capacitor 178 to the base of the high gain third amplifier stage transistor 179. Since capacitor 178 blocks any d-c potential which may exist on the collector of transistor 171, a d-c bias is established upon the base of transistor 179 by a resistor 181 to the negative terminal 130. The third stage transistor 179 in conjunction with an emitter resistor 183 to the common terminal 131 and a collector load resistor 184 to the positive terminal 130 amplifies the a-c signal and applies it through a coupling resistor 186 and capacitor 187, in parallel, to the base of a transistor 190 biased to exhibit high gain for shaping the input pulses. The base-emitter bias of pulse shaping transistor 190 is maintained by resistor 191 between the base and the common terminal 131. The positive portion of the output signal developed across the collector resistor 193 to the positive terminal 130 is coupled by a capacitor 195 and a resistor 196 connecting the low side of the capacitor 195 to the negative terminal 130 to the monostable 123 through a coupling diode 198.

The monostable 123 includes two transistors 200 and 201. A positive pulse from the fourth transistor stage of the amplifier section 122 is applied to the base of transistor 200 to forward bias its emitter-base junction into conduction. When the transistor 200 conducts, the voltage upon series connected voltage divider resistors 206 and 207 drops, presenting a more negative voltage upon the base of transistor 201 to forward bias that transistor into conduction through its collector resistor 211, thereby charging capacitor 204 through resistor 210 and further forward biasing the transistor 200. When the charge on capacitor 204 discharges, the bias upon the base of transistor 200 established by resistor 212 is reduced, causing the transistor 200 to fall back into nonconduction, which, in turn, raises the voltage developed across resistor 206, causing the transistor 201 also to lapse into nonconduction.

The output voltage from the monostable 123 developed across resistors 206 and 207 is coupled by a capacitor 215 into the disabling circuit 124 to be applied through series connected voltage dividing resistors 217 and 218 to the base of transistor 220, causing it to conduct. At the same time, the conduction current through transistor 220 is coupled by resistor 222 to the base of the second transistor 224 causing it also to conduct. The respective collectors and emitters of transistors 220 and 224 are connected in parallel with the timing capacitors 137 and 146 of the free running multivibrator stage 120, to provide a discharge path for the capacitors when the transistors 220 and 224 are biased into conduction upon the arrival of a pulse from the monostable 123.

To add a time delay to the pulse traversing the amplifier 122, monostable 123, and disabling circuit 124, a capacitor 230 is provided between the base of transistor 220 and the common terminal 131. Thus, the output pulse from the outpulse stage 121, as fed back to the input of the frequency selective amplifier section 122 will not prematurely disable the free running multivibrator 120.

A zener diode 232 is provided between the output terminal 149 to the common terminal 131 to permit application of a fillibration or other external voltage to the patient without overloading the devices of the pacer circuitry. Thus, if a voltage of positive polarity is applied to the output terminal 149, it is immediately bypassed to the common terminal 131. On the other hand, if a negative voltage above the breakdown voltage of the zener diode 232 is applied, it will be also bypassed to the common terminal 131.

As above mentioned, the pacer circuit of FIG. 2 is intended for use with a nuclear battery (not shown). A suitable nuclear battery may be such as that described by Steve A. Kolenik and Thomas F. Hursen, *Nuclear Energy Sources*, 167 Annals of the New York Academy of Sciences, October 30, 1969, pp. 661 et seq.; and by S. A. Kolenik, T. F. Hursen, and G. W. Maurer, *Radioisotope Powered Pacemaker Development Program*, Annual Winter Meeting of the American Nuclear Society, Oct. 18, 1971; and in U.S. Pat. No. 3,649,367. Because the nuclear battery may have a relatively high resistance, on the order of 5K–11K ohms to be applied to terminal 130, a relatively large capacitor 234 is connected between the battery terminals 130 and 131 to reduce IR losses in the battery during high instantaneous current demands in the circuit, for example, when the free running multivibrator stage 120 conducts. Thereafter, upon demand of the circuit upon the voltage source, the current may be obtained from both the battery itself and from the discharge current from the capacitor 234. It should also be noted that nuclear batteries typically have a voltage characteristic in which an increasing load upon the battery results in decreased output voltage. Consequently, the capacitor 234 assures proper circuit operating voltage regardless of the instantaneous load applied to the battery terminals 130 and 131.

Finally, to permit the free running multivibrator and output amplifier sections to be tested, a magnetic switch 236 is provided between the base of transistor 220 and the common terminal 131. To test the operation of the circuit, therefore, a magnetic field can be applied to the patient wearing the heart pacer circuit to close the magnetic switch 236 and disable the transistors of the disabling section 124. The free running multivibrator, therefore, will independently pulse without being disabled and can be detected to assure proper multivibrator, voltage source, and output amplifier operation.

In the circuit of FIG. 2, by way of example, it has been found that the following component types and values result in proper circuit operation.

| Resistors (ohms) | |
|---|---|
| 135,140 | 1.8M |
| 136,141 | 680 |
| 144 | 22K |
| 145,151, 152,172 | 47K |
| 153 | 120 |
| 158 | 27K |
| 160,164, 173 | 10K |
| 168,175, 193,222 | 100K |
| 167,210 | 470K |
| 176,186, 191,196, 212 | 1.5M |
| 181 | 6.8M |
| 183 | 39K |
| 184,206 | 150K |
| 207 | 390K |
| 211 | 560K |
| 217 | 210K |
| 218 | 120K |
| Capacitors (microfarads) | |
| 137,146, 165,169, | 0.47 |
| 174,215 150,159 | 39 |
| 178,187, 195,204 | 0.047 |
| 230 | 0.02 |
| 234 | 120 |
| Diodes | |
| 198 | 1N3010 |
| 232 (zener) | IN756A |
| Transistors | |
| 131,166, 179,190, 201,220 | 2N2907A |
| 133,148, 155,171, 200 | 2N222A |

It is apparent from the circuit of FIG. 2, above described, that the transistors of different conductivity type (n-p-n, p-n-p, etc.) may be substituted into the circuit with appropriate modification in the supply voltage polarity and associated component values. It should also be appreciated that although the circuitry has been illustrated and described with respect to transistors, that any solid state device, such as integrated circuits, single circuit semi-conductor chips, and the like, can be advantageously employed with appropriate circuit value modifications, as will be apparent to those skilled in the art. It should also be pointed out that although the components listed above described particular types of transistors, that any transistor having the same functional characteristics can be employed, again with appropriate associated component adjustment for proper biasing and operation.

Although the circuitry of the invention has been described and illustrated with a certain degree of particularity, it is understood that the present disclosure is made by way of example only and that numerous changes and modifications will become apparent to those skilled in the art without departing from the spirit and scope of the invention as hereinafter claimed.

I claim:

1. Apparatus for generating electrical heart stimulation pulses adapted to be connected to pulse delivery electrodes, at least one of which being connectable to a heart, comprising:
   a free running multivibrator for generating electrical pulses at a rate desired for heart stimulation in the absence of natural heart pulses, said free running multivibrator including plural identical timing circuits, each comprising a resistor and a capacitor in series, each timing circuit capable of triggering said free running multivibrator to initiate a pulse,
   a high impedance voltage doubler output stage connected to said pulse delivery electrodes to which the generated pulses are applied to produce corresponding output pulses upon said delivery electrodes,
   a frequency filtering amplifier for amplifying signals detected upon said delivery electrodes within a selected frequency spectrum,
   means for generating a signal connected to said amplifier for producing a control signal in response to signals amplified by said amplifier, and for blocking additional signals amplified by said amplifier for a predetermined refractory period,
   means connected across each of said capacitors of said plural timing circuits activated by said control signals for selectively discharging each of said capacitors to cancel a free running multivibrator generated pulse, and
   delay means interconnected between said control signal generating means and said capacitor discharging means to prevent a stimulation pulse from prematurely discharging said capacitors of said timing circuits before the termination of the stimulation pulse.

2. The apparatus of claim 1 wherein said free running multivibrator is normally nonconducting and wherein said plural timing circuits each comprises a pair of resistor-capacitor timing circuits, the voltage on each of the capacitors controlling the initiation of conduction of the free running multivibrator to generate an electrical pulse and discharge the capacitors.

3. The apparatus of claim 2 wherein said means for generating a control signal and for blocking additional signals in response to amplified signals upon said electrodes comprises:
   a normally nonconducting monostable multivibrator for generating a voltage pulse when triggered by an amplified signal from said frequency filtering amplifier, applied to said monostable multivibrator.

4. The apparatus of claim 3 wherein said frequency filtering amplifier amplifies electrical signals having primarily the same frequency spectra as a naturally occurring "R" wave.

5. The apparatus of claim 4 wherein said means for discharging said capacitors of said timing circuits comprises a transistor for each of said capacitors, the collector and emitter of which shunts the capacitor, and the base of which is connected to said delay means to receive the pulse from said monostable multivibrator to bias said transistor into conduction to discharge said capacitor.

6. A demand pacer for supplying a heart stimulation pulse in the absence of a naturally generated "R" wave, comprising:

a. pair of electrodes, at least one of which is adapted to be connected to the heart;
b. a free running multivibrator for generating electrical pulses, including a pair of identical timing circuits each comprising a resistor and a capacitor in series, each timing circuit for independently controlling the pulse repetition rate of the free running multivibrator;
c. an amplifier connected to said free running multivibrator to receive the pulses generated thereby for amplifying the generated pulses;
d. a voltage doubler circuit connected to said amplifier and to said electrodes to develop an electrical current upon said electrodes for application to the heart;
e. An amplifier connected to said electrodes for detecting and selectively amplifying electrical signals upon said electrodes of frequency within the frequency spectrum of the "R" wave, including:
   1. a capacitor in series with one of said electrodes for differentiating the electrical signals applied thereto from the heart,
   2. two Class A amplifier stages for amplifying the differentiated signal, one stage having a low frequency roll off characteristic below the "R" wave frequency spectrum, and the other stage having a high frequency roll off characteristic above the "R" wave frequency spectrum,
   3. a high gain third amplifier stage a-c coupled to said two amplifier stages for further signal amplification, and
   4. a pulse shaping circuit for enhancing the pulse shape of the differentiated and amplified signal, said capacitor, two Class A amplifiers, third amplifier, and pulse shaping circuit being serially connected to sequentially operate upon a detected signal on said electrodes;
f. a monostable multivibrator connected to said pulse shaping circuit, triggered by the differentiated, amplified, and shaped signal for generating an output pulse to block additional signals on said electrodes when said monostable multivibrator is in a conducting state to define a refractory period;
g. transistor switch means for shorting the capacitors of the free running multivibrator to discharge the capacitors, said transistor switch means being controlled by the output pulses from said monostable multivibrator, and
h. delay means interconnecting an output of said monostable multivibrator and said transistor switch means to delay the output pulse of said monostable multivibrator, whereby a pulse generated by said free running multivibrator is allowed to terminate prior to the capacitors thereof being discharged by said transistor switch means.

7. The demand pacer of claim 6 wherein said free running multivibrator comprises:
   two transistors, each having an emitter, base, and collector, of opposite conductivity type, said two transistors being normally nonconducting in the absence of an output pulse,
   first and second resistor means interconnected between the collector and base of a respective one of said two transistors, and wherein said pair of timing circuits are each connected between the base of a respective one of said two transistors and the collector of the other.

8. The demand pacer of claim 7 further comprising a nuclear powered source of electrical potential connected to the demand pacer to supply electrical power thereto.

* * * * *